US00PP08396P

United States Patent [19]

Drewlow

[11] Patent Number: Plant 8,396

[45] Date of Patent: Sep. 28, 1993

[54] IMPATIENS PLANT NAMED RHAPSODY

[75] Inventor: Lyndon W. Drewlow, Ashtabula, Ohio

[73] Assignee: Mikkelsens, Inc., Ashtabula, Ohio

[21] Appl. No.: 858,087

[22] Filed: Mar. 26, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A distinct cultivar of Impatiens plant named Rhapsody, characterized by its very large deep reddish purple flowers, overlapped petals which give the flower a more rounded appearance, early blooming habit, and its relatively large green leaves with no variegation.

1 Drawing Sheet

The present invention relates to a new and distinctive cultivar of Impatiens plant, botanically known as Impatiens, commercially known as New Guinea Impatiens, and known by the cultivar name Rhapsody. Rhapsody was developed by me through controlled breeding by crossing Veronika with Mikkelsen Seedling No. 89-512-6.

Asexual reproduction by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry. The cultivars Antares (U.S. Plant Pat. No. 7,241) and Veronika are referred to for comparison purposes.

1. Rhapsody has deep reddish purple flowers (61B) which are much darker in color than the deep lilac flowers (72C to 77B) of Antares and Veronika (78B). No Impatiens cultivar has this unique color to the best of my knowledge.

2. Rhapsody has a much larger flower (6.5 to 7.0 cm) than either Veronika or Antares both of which have flowers which are 4.5 to 5.0 cm in diameter.

3. The flowers of Rhapsody appear much rounder than either Veronika or Antares as there is more overlap of petals, especially between the standard and wings. Veronika and Antares have flowers which have almost no overlap between the standard and wings.

4. The flower pedicel of Rhapsody is reddish purple in color which is similar to Veronika, while Antares has a green colored pedicel.

5. Rhapsody is 4 to 7 days earlier to bloom than either Veronika or Antares.

6. Rhapsody has solid green leaves while both Antares and Veronika have cream colored variegation around the midrib on the basal part of the leaf, especially under high light.

7. The younger leaves especially of Rhapsody have a reddish midrib and major veins on the underside of the leaf. This feature is similar to Veronika, with Antares having a green midrib and veins.

8. Rhapsody has larger leaves at 14 to 15 cm long and 4.5 to 5.0 cm wide than Antares at 8 to 9 cm long and 2 to 3 cm wide, or Veronika at 10 to 11 cm long and 3.5 to 4.0 cm wide.

9. Rhapsody is intermediate in red stem coloration between Veronika, which has the most red coloration in stem tissue, and Antares which has the least.

10. Both Rhapsody and Veronika have a reddish purple flower spur with a deeper reddish purple tip, while Antares has a lighter red spur with a green tip.

The accompanying color photograph is a front perspective view showing the overall appearance of Rhapsody, with the colors being as nearly true as is reasonably possible to obtain in a colored reproduction of this type. The photograph was taken on Apr. 15, 1991 under natural light on an overcast day, with the plant being photographed under double poly greenhouse covering at Ashtabula, Ohio.

The following is a detailed description of my new cultivar, based on plants produced in greenhouses in Ashtabula, Ohio during the Fall and early Winter seasons of the year. Plants were grown in 10 cm pots and measurements were taken 12 weeks after rooted cuttings were planted. Height measurements were taken from the soil line of the container. The plants were grown at 68°-68° F. night temperatures, under 3000-4000 foot candles of light, and with nutritional values of 250 ppm nitrogen, 75 ppm potassium, and 250 ppm phosphorous, with trace elements added. Habit of growth, foliage coloration, leaf variegation, size of leaves and flower size will be influenced by nutritional and environmental conditions, without, however, any variation in the phenotype.

Color references are made to the Royal Horticultural Society Colour Chart except where general terms of ordinary dictionary significance are used.

Parentage: A controlled cross between female parent Veronika and male parent Mikkelsen Seedling No. 89-512-6.

Propagation:

A. *Type cutting.*—Stems 15 mm long will develop 4 to 5 cm long in 18 to 21 days.

B. *Time to root.*—8-10 days at 23° C. summer; 10-12 days at 20° C. winter.

C. *Rooting habit.*—Heavy, fibrous.

Plant description:

A. *Form and habit of growth.*—Semi-upright, self-branched, intermediate in height, flowers over top of leaf canopy; continuous flowering; vigorous growing flowering herb.

B. *Foliage description.*—Dark green, pinkish cast to midrib and no variegation on leaves. 1. Size: 14 to 15 cm long and 4.5 to 5.0 cm wide on average mature leaves. 2. Shape: Lanceolate with acuminate apex and acute base. 3. Texture: Both upper and lower surfaces are glabrous. 4. Margin: Finely serrated with fine cilate. 5. Color: Young foliage, top side 137A; under side 147C. Mature foliage, top side 147A; under side 147B. 6. Venation: Pinnate, reddish purple in color.

Flowering description:

A. *Flowering habits.*—Flowers continuously from leaf whorl in a progressively orderly manner with one flower per leaf axil. When the last flower in a leaf whorl opens, the first flower in the leaf whorl above starts to open. It takes 5 to 7 days for a mature bud to fully open and then the flower may last 2 weeks or longer depending on the environment.

B. *Natural flowering season.*—Indeterminant and continuous. Quantity of flowering increases with increasing levels of light.

C. *Flower buds.*—Ellipsoidal; flowers perfect; reddish purple spur 6.0 cm long on mature bud with the throat behind the ovary and originating from the major sepal.

D. *Flowers borne.*—Individual reddish purple pedicels (4 cm) from a whorl of 5 to 6 leaves, flowering progressively around the whorls as buds and leaves develop. Leaf axils have one flower each.

E. *Quantity of flowers.*—Numerous because of highly self-branched nature of plant and long lasting flowers, with flowers open at 2 leaf whorls on a branch. Flower development is continuous and above leaf canopy.

F. *Diameter of flower.*—6.5 to 7.0 cm.

G. *Petals.*—1. Shape: Heart; two keel petals and standard are very similar in size and larger than wings. 2. Color: Top side in winter when opening, 61B, fading to 67B; underside 67B to 67C. 3. Number of petals: 5. 4. Size of petals: Standard: 4.0 cm wide by 3.0 cm long; two equal lobes, almost no cut. Wings: 2.5 cm wide by 3.0 cm long; two unequal lobes, intermediate cut. Keel: 3.5 cm wide by 3.5 cm long; two unequal lobes deeply cut.

H. *Reproductive organs.*—1. Stamens: Five (5) in number. a. Anther shape: Hooded, color white with heavy purple tint. b. Pollen color: Cream. 2. Pistils: a. Stigma shape: Five (5) segmented column. b. Style color: White. c. Ovaries: Five (5) in number, size 5 mm (mature), color: green.

Disease resistance:

No significant disease or insect problems noted to date.

Other Important Characteristics

1. Self-branching, early flowering nature allows cultivar to be grown in 10 cm pots. However, Rhapsody is also vigorous so it can be grown in 15 to 25 cm containers.

2. Rhapsody has shown the ability to tolerate both high temperatures and sunlight and continue to bloom, as well as cool temperatures (40°-50° F.). Thus growing season has been expanded.

I claim:

1. A new and distinct Impatiens plant named Rhapsody, as illustrated and described.

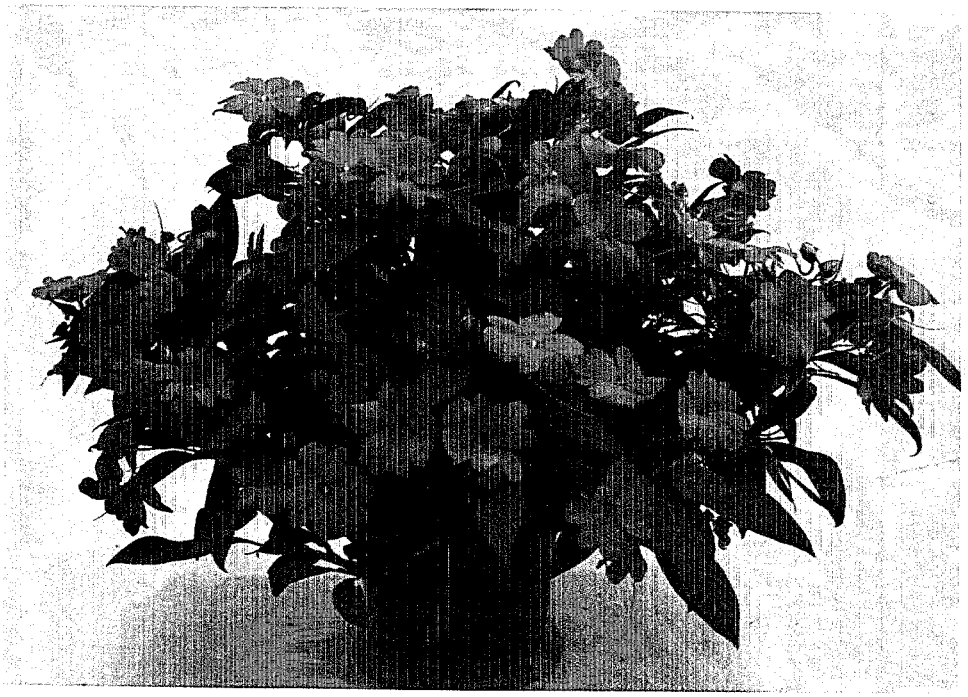

* * * * *